United States Patent [19]

Torikai

[11] Patent Number: 4,693,953
[45] Date of Patent: Sep. 15, 1987

[54] METHOD FOR PRODUCTION OF MOISTURE SENSITIVE ELEMENT

[75] Inventor: Eiichi Torikai, Yao, Japan

[73] Assignee: Agency of Industrial Science & Technology, Ministry of International Trade & Industry, Tokyo, Japan

[21] Appl. No.: 845,510

[22] Filed: Mar. 28, 1986

[30] Foreign Application Priority Data

May 17, 1985 [JP] Japan .................................. 60-106729

[51] Int. Cl.⁴ .................... G03C 1/52; G03C 5/00; B01D 59/40

[52] U.S. Cl. .................................. 430/165; 430/5; 430/190; 430/296; 430/320; 430/323; 430/325; 430/326; 430/330; 204/1 T

[58] Field of Search .................. 430/5, 165, 166, 190, 430/191, 296, 320, 323, 325, 326, 330; 204/1 T

[56] References Cited

U.S. PATENT DOCUMENTS

| | | |
|---|---|---|
| 4,083,765 | 4/1978 | Lawson .......................... 204/195 W |
| 4,343,885 | 8/1982 | Reardon, Jr. ........................ 430/177 |
| 4,361,950 | 12/1982 | Amick .................................... 29/572 |
| 4,376,030 | 3/1983 | Ezzell et al. ......................... 204/296 |
| 4,386,336 | 5/1983 | Kinomoto et al. .................... 338/35 |
| 4,391,845 | 7/1983 | Denley ................................... 427/58 |
| 4,528,543 | 7/1985 | Miyoshi et al. ....................... 338/35 |
| 4,529,642 | 7/1985 | Miyoshi et al. ..................... 428/201 |
| 4,552,830 | 7/1985 | Reardon et al. .................... 430/281 |
| 4,595,476 | 6/1986 | Bissot ................................. 204/252 |

*Primary Examiner*—John E. Kittle
*Assistant Examiner*—Patrick J. Ryan
*Attorney, Agent, or Firm*—Oblon, Fisher, Spivak, McClelland, & Maier

[57] ABSTRACT

A moisture-sensitive element is produced by applying an ultraviolet-setting alkali-elution type resist ink on a prescribed part of a cation-exchange membrane, curing and drying the applied layer of the resist ink, chemically plating the cation-exchange membrane thereby forming electrode layers thereon, and thereafter removing the resist ink from the cation-exchange membrane.

8 Claims, 4 Drawing Figures

FIG_1
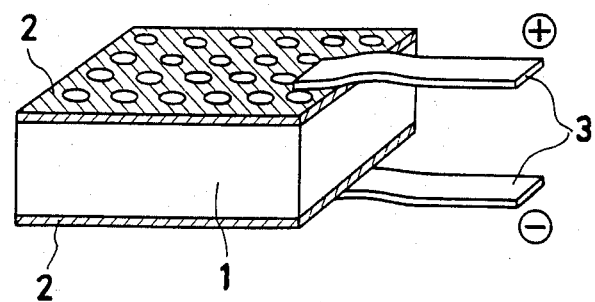
FIG_2
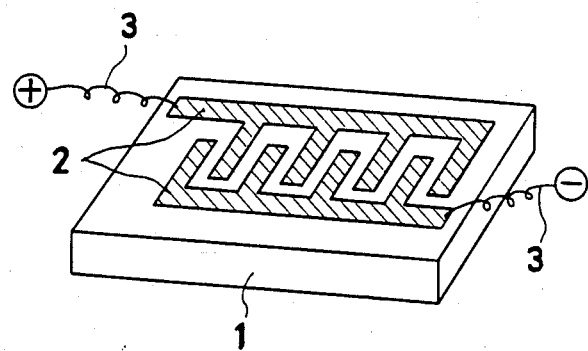

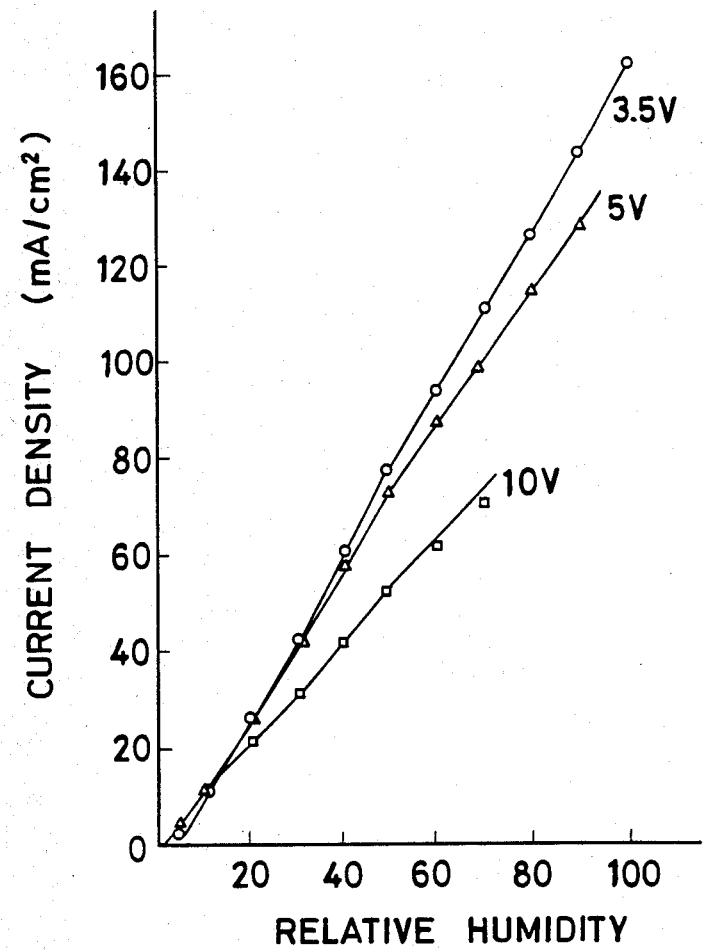
FIG_3

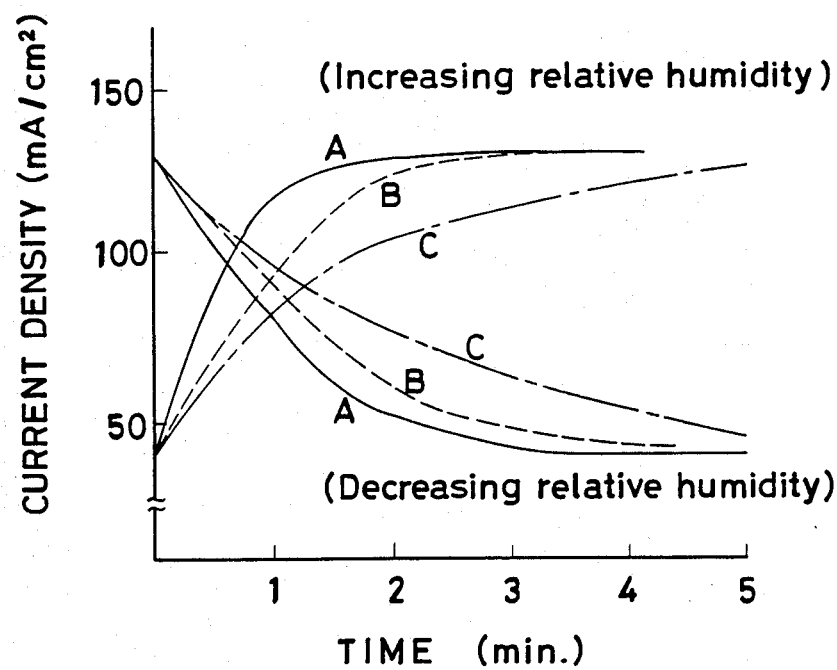
FIG_4

METHOD FOR PRODUCTION OF MOISTURE SENSITIVE ELEMENT

FIELD OF THE INVENTION AND RELATED ART STATEMENT

This invention relates to a method for the production of a moisture-sensitive element excelling in response characteristic, exhibiting stable performance, and enjoying a long service life.

As means of measuring humidity in a gas, a method which determines the humidity by utilizing the principle of electrolysis of water has been known to the art. U.S. Pat. No. 4,083,765, for example, discloses a method which accomplishes the determination of humidity with a sensor comprising a tube made of a fluorine resin possessing a perfluorosulfonate group and coils of platinum held in intimate contact with the inner and outer walls of the tube to serve as electrodes. This method has a disadvantage that the output current is small because the reaction for decomposition of water occurs only in the parts of contact between the fluorine resin tube and the coiled electrodes and the contact resistance is large because the current concentrates on the points of contact between the tube and the coil. It has another disadvantage that since the contact between the tube and the coiled electrodes cannot be easily maintained in a uniform state over protracted service, the output current varies with the change in the contact resistance and the reliability of performance is poor. There is also a possibility that, in a highly humid condition, the magnitude of the current will increase and, as a result, the heat generated by the resistance at the points of contact will deteriorate the tube.

Japanese Patent Public Disclosure No. SHO 60(1985)-36947 discloses a method which effects the determination of humidity by using as a moisture-sensitive element a composite comprising an ion-exchange membrane and electrodes attached fast one each to the opposite surfaces of the ion-exchange membrane. This method is free from the problem of contact resistance encountered by the U.S. patent mentioned above because it uses electrodes possessing satisfactory permeability to gas and high electroconductivity. It nevertheless has a disadvantage that it responds poorly to variation in the humidity of the ambient air because the parts of the ion-exchange membrane available for absorption of water are small.

OBJECT AND SUMMARY OF THE INVENTION

An object of this invention is to provide a moisture-sensitive element which is free from the drawbacks suffered by the conventional moisture-sensitive elements, i.e. which has satisfactory response characteristics, exhibits stable performance, and enjoys a long service life.

The inventor, after various studies directed to achieving of the object described above, has found that a moisture-sensitive element obtained by using a cation-exchange membrane capable of migration of hydrogen ion, masking a stated part of the cation-exchange membrane with an ultraviolet-setting, alkali-elution type resist ink, then chemically plating the cation-exchange membrane thereby forming electrodes on the exchange membrane, and subsequently removing the resist ink exhibits a satisfactory response characteristic to variation in the humidity of the ambient air because the stated part of the cation-exchange membrane is left exposed and, therefore, enabled to function as a part for the adsorption of water and issues the output current stably and enables the humidity to be determined accurately for a long time, because the electrode layer adheres to the cation exchange membrane. This invention has been perfected as the result.

To be specific, this invention relates to a method for the production of a moisture-sensitive element characterized by the steps of applying an ultraviolet-setting, alkali-elution type resist ink on a prescribed part of a cation-exchange membrane, causing the applied layer of the resist ink to cure, then chemically plating the cation-exchange membrane thereby forming electrode layers on the cation-exchange membrane, and thereafter removing the resist ink.

BRIEF DESCRIPTION OF THE DRAWINGS

FIGS. 1 and 2 are perspective views illustrating typical moisture-sensitive elements obtained by the method of this invention.

FIG. 3 is a graph showing the relation between the relative humidity and the current density obtained by varying the voltage applied to a moisture-sensitive element produced by the method of this invention in Test Example 1.

FIG. 4 is a graph comparing a moisture-sensitive element produced by the method of this invention in Test Example 2 and a moisture-sensitive element produced by a method not conforming with this invention, in terms of response characteristics.

DETAILED DESCRIPTION OF THE PREFERRED EMBODIMENT

In this invention, any of the $H^+$ ion conductors can be used as the cation-exchange membrane. The cation-exchange membrane is desired to possess chemical stability, resistance to oxidation, mechanical strength, and thermal resistance. Particularly, an exchange membrane using a carbon fluoride polymer as a substrate and possessing a sulfonate group or a carboxylate group as an exchange group or a composite membrane incorporating the exchange membrane just mentioned proves desirable. As concrete examples of the cation-exchange membrane answering the description, commercial products of DuPont marketed under trademark designation of "Nafion 125, 117, 120, ..." and commercial products of Asahi Glass marketed under trademark designation of "Fremion" may be cited, all of which are perfluorocarbon sulfonate.

In this invention, it is desirable for the cation-exchange membrane to be roughened for the purpose of enhancing intimate adhesion of the resist ink and the plating metal to the membrane before the membrane is masked with the resist ink. This roughening can be accomplished by any of the conventional methods such as sand blasting, liquid honing, plasma treatment, and sputter etching. The cation-exchange membrane which has been roughened is desired to be converted to the $H^+$ form by the conventional method. This conversion to the $H^+$ form can be accomplished, for example, by heating the cation-exchange membrane in an aqueous 10% HCl solution, then boiling it in pure water, and drying the wet membrane.

The resist ink to be used in this invention is required to be of an ultraviolet-setting alkali-elution type. Heretofore, the method of masking an ion-exchange membrane with a resist ink has never been carried out because it is difficult to be masked clearly since the solvent, the reacting agent, etc. contained in the resist ink swell and inactivate the exchange membrane and the heat generated during the curing deforms the exchange membrane. It has been ascertained by the inventor that so long as the resist ink is of the ultraviolet-setting alkali-elution type, it deforms and swells the ion-exchange membrane minimally and avoids polluting or damaging such active groups of the ion-exchange membrane as —SO₃H and —COOH. If the resist ink to be used is of a thermosetting type, it causes heavy deformation of the membrane during the course of thermosetting. If the resist ink is of a solvent separation type, it pollutes the active group of the ion-exchange membrane.

This invention is characterized particularly by using the resist ink of the type described above.

A part defying deposition of a chemically plating layer can be formed on a cation-exchange membrane through inactivation of such exchange groups of the cation-exchange as —SO₃H and —COOH by irradiation of electron beam, plasma treatment, or sputter etching without using any resist ink. This method, however, fails to achieve its object because the exchange groups in the inactivated part are liable to be destroyed and the produced moisture-sensitive element possesses an insufficient capacity for water adsorption.

In this invention, the resist ink applied on the ion-exchange membrane is required to defy deposition of any metal thereon when the ion-exchange membrane undergoes a chemical plating. To fulfill this requirement, the resist ink suitably is of a type such that polar groups such as hydroxyl group, carboxyl group, and melamine group do not remain in the applied layer of the resist ink after drying. When such polar groups remain in the applied layer after drying, it is required to incorporate therein approximately 0.02 to 0.5%, preferably 0.05 to 0.1%, of a sulfur type inhibitor such as thiourea or mercaptan which functions as a poison to the chemical plating.

This invention permits use of any of the conventional resist inks which satisfy the aforementioned properties. For example, it can use any ordinary resist ink which is composed of a prepolymer resin, a cut polymer, a photo-initiator, and an extender. As concrete examples of the prepolymer resin for the resist ink suitably used in the method of this invention, epoxy acrylate, alkyd acrylate, polyester acrylate, polyol acrylate, polyether acrylate, oligoacrylate, and polyurethane acrylate may be cited. As concrete examples of cut monomers, there may be cited monoacrylates, diacrylates, and triacrylates such as 1,6-hexadiol monoacrylate, cyclohexyl acrylate, 1,6-hexanediol acrylate, neopentyl glycol diacrylate, trimethylol propane triacrylate, and pentaerythritol triacrylate. Examples of photo-initiators include such initiators as benzoin compounds, acetophenone compounds, and ketone-amine compounds. Examples of extenders usable advantageously herein include precipitated barium sulfate and aerosil.

It is necessary that the resist ink should be applied to a prescribed part of the cation-exchange membrane. After completion of the chemical plating in the next step, the applied layer of the resist ink is peeled off to expose the prescribed part of the cation-exchange membrane. The exposed part of the cation-exchange membrane functions as the part of the moisture-sensitive element for adsorption of water. As compared with the conventional moisture-sensitive element which has electrodes formed on the entire surface of an exchange membrane, the moisture-sensitive element of this invention has a larger capacity for the adsorption of water and enjoys better response to variation in the humidity and higher accuracy of determination of the humidity.

The area for application of the resist ink on the cation-exchange membrane, on the side of the membrane destined to function as an anode for the electrolysis of water, is approximately 20 to 80%, preferably 30 to 50%, of the area of the exchange membrane. On the anode side, the part does not permit deposition of an electrode thereon but functions as a part for the adsorption of water. Thus, the produced moisture-sensitive element enjoys improved response to variation in the humidity.

On the side of the cation-exchange membrane which is destined to function as a cathode when the produced moisture-sensitive element is put to use, the entire surface may be chemically plated to form an electrode instead of being coated with the resist ink. Even on this side, however, the resist ink may be applied on a prescribed part of the membrane and, after completion of the chemical plating, the applied layer of the resist ink may be peeled off to expose the prescribed part of the membrane as contemplated by the present invention. In this case, the area of the part so exposed has to be not more than about 80% of the entire cathode side of the membrane. If the exposed area of the exchange membrane on the cathode side increases and the part of the electrode decreases excessively, there ensues a disadvantage that the contact resistance increases. The exposure of the exchange membrane on the cathode side thereof does not constitute any indispensable requirement for this invention. The exposure effected on the cathode side of the exchange membrane by the method of this invention, however, serves to increase the capacity of the produced moisture-sensitive element for the adsorption of water and enhance the response of this element to variation in the humidity.

The manner in which the resist ink is applied is not specifically limited. The screen printing method proves desirable because it enables the resist ink to be easily applied in any desired shape. The shape to be assumed by the applied resist ink is not specifically limited. The resist ink may be suitably applied in a desired pattern such as a circle, an ellipsis, a polygon, or comb teeth.

After the resist ink is applied, the applied layer of the resist ink is cured by exposure to ultraviolet light and then dried. The exposure to ultraviolet light can be carried out under the conventional conditions. When a high-pressure mercury vapor lamp (output 80 W/cm) is used as the source for violet light, for example, the exposure time is in the range of 2 to 10 seconds, preferably 3 to 5 seconds.

After the cation-exchange membrane is masked with the resist ink, it is chemically plated to give rise to an electrode layer on the cation-exchange membrane. The material for the electrode layer is only required to be electrochemically stable. Since the cation-exchange membrane is generally acidic, this material is desired to be a platinum type metal such as Pt or Rh or an alloy thereof from the standpoint of acidproofness and chemical stability.

The chemical plating of the exchange membrane can be carried out by any of the conventional methods. For example, the methods developed by the inventors and disclosed in Japanese Patent Publication No. SHO 58(1983)47471, Japanese Patent Publication No. SHO 59(1984)-39504, Japanese Patent Publication No. SHO 59(1984)-33667, and Japanese Patent Publication No. SHO 59(1984)-34784 are available.

The electrode layer to be formed is required to have enough thickness to ensure sufficient electroconductivity and satisfactory intimate adhesiveness. Generally, this thickness falls in the range of about 1 to 5 $\mu$m.

Since the electrode layer formed by the chemical plating adheres intimately to the cation-exchange membrane, the output current is highly stable. The contact resistance generated by the electrode layer with the exchange membrane is small because the area of contact between the electrode layer and the cation-exchange membrane is large and the electrode layer enjoys satisfactory electroconductivity. As a result, the exchange membrane is enabled to maintain its stable performance intact for a long time because it has no possibility of being deteriorated by the heat generated otherwise by the contact resistance.

A typical plating method usable for the formation of a platinum layer as an electrode will be cited below.

First, a cation-exchange membrane having a layer of a resist ink deposited thereon is immersed in an ammine complex salt solution of platinum containing about 0.5 to 5 mg/ml of platinum for 1 to 10 hours, preferably 2 to 3 hours. Then, the cation-exchange membrane is washed with water and immersed in a 0.05 to 0.5% hydrogenated sodium borate solution at room temperature to 50° C. to cause reducing precipitation of a Pt layer 0.1 to 1 $\mu$m in thickness. Subsequently, the treated membrane is placed in a solution consisting of an ammine complex salt of platinum, hydroxylamine, hydrazine, and a small amount of aqua ammonia and subjected to chemical plating at 50° to 60° C. to form an electrode made of a platinum layer 1 to 5 $\mu$m in thickness.

After completion of the plating treatment, the resist ink is separated from the membrane with an aqueous alkali solution. The concentration of this aqueous alkali solution is variable with the composition of the resist ink. Generally, use of a sodium hydroxide solution of a concentration of 2 to 5N suffices. The speed of separation of the resist ink may be heightened by adding a small amount of hydrogen peroxide to the aqueous alkali solution.

After the separation of the resist ink, the cation-exchange membrane is converted to the $H^+$ form by the conventional procedure which comprises heating the membrane in an aqueous solution of about 10% of HCl, then boiling the membrane in pure water, and drying the boiled membrane at a temperature not exceeding 60° C. The resulting $H^+$ form cation-exchange membrane is used as a moisture-sensitive element.

The surface size of the moisture-sensitive element to be obtained by the method of this invention is not specifically limited. Generally, a sufficient surface size of the element is about 0.1 to 1.0 cm$^2$. The element of an excessively large surface size not only proves uneconomical but also entails a disadvantage that the amounts of hydrogen and oxygen to be produced increase to a point where the equilibrium of steam surrounding the moisture-sensitive element is disturbed.

Now, the method for determination of humidity by the use of the moisture-sensitive element produced by the present invention will be described below with reference to the accompanying drawings.

First, terminals for power supply are disposed one each on the opposite sides of a cation-exchange membrane provided in advance with electrodes as illustrated in FIG. 1, to apply a DC voltage thereon. With reference to FIG. 1, 1 stands for a cation-exchange membrane, 2 for electrode layers, and 3 for power supply terminals. When a resist ink is applied on only one side and treated to expose the covered part of the membrane and no resist ink is applied on the other side and an electrode layer is formed throughout the entire surface of this side, the side containing the exposed part of the cation-exchange membrane is used as an anode and the side having the electrode layer formed throughout the entire surface thereof is used as a cathode. When the application of the resist ink and the subsequent chemical plating are carried out on only one side, both an anode and a cathode may be formed on one and the same side of the exchange membrane as illustrated in FIG. 2. With reference to FIG. 2, 1 stands for a cation-exchange membrane, 2 for electrode layers, and 3 for power-supply terminals. The resist ink has to be applied on the part other than the part covered with the electrode layers.

In the moisture-sensitive element of this invention, when a DC voltage is applied to the electrode layers, the reaction, $H_2O \rightarrow 2H^+ + \frac{1}{2}O_2 + 2e$, occurs at the anode and the produced $H^+$ flows through the cation-exchange membrane and reaches the anode and induces the reaction, $2H^+ + 2e$, there. Since the amount of the electric current which flows at this time is exactly proportional to the amount of water which is electrolyzed, the humidity of the ambient air can be determined by measuring the magnitude of the electric current.

The theoretical decomposition voltage of water is 1.23 V (25° C.). Thus, the electric current increases in proportion as the applied voltage is increased beyond 1.23 V. The magnitude of the electric current no longer increases when the applied voltage is increased beyond the specific voltage at which the speed of adsorption of water by the exchange membrane and the speed of electrolysis of water are equilibrated. The current density existing at this specific voltage is the so-called critical current density. This critical current exhibits a proportional relation with the humidity. Since the voltage which gives this critical current density generally exceeds 2 V, it suffices to fix the applied voltage beyond 2 V, preferably beyond 3 V. To be specific, the applied voltage may be fixed at a level such that the magnitude of electric current and the humidity exhibit a satisfactory proportional relation, with due respect paid to the humidity prevalent in the ambient air under test.

The present invention brings about the following conspicuous effects.

1. Since a fixed area of the cation-exchange membrane is exposed to the ambient air, the moisture-sensitive element has a large capacity for the adsorption of water, excels in response to variation in the humidity of the ambient air, and determines the humidity with high accuracy.

2. Since the electrode layer is allowed to adhere with high intimacy to the cation-exchange membrane by the chemical plating, the moisture-sensitive element enjoys high stability of the output current.

3. The electrode layer has a large area of contact with the cation-exchange membrane and possesses satisfactory electroconductivity. Thus, the contact resistance generated between the electrode layer and exchange membrane is small enough to preclude the otherwise possible deterioration of the exchange membrane by heat.

4. A continuous electrode layer can be formed on the surface of the membrane as illustrated in FIG. 1. If a disconnection occurs in part of the electrode layer as by cracking, it has substantially no adverse effect on the electrochemical stability. Because of the continuity of the electrode layer, the attachment of the terminals can be easily effected.

5. Since the moisture-sensitive element of the present invention accomplishes the determination of humidity by utilizing the electrolysis of water, it can be used effectively for the purpose of dehumidification. In this case, the element need not be limited to the small surface size but may be produced in any desired surface size suitable for dehumidification.

Now, the present invention will be described more specifically below with reference to working examples.

EXAMPLE 1

A perfluorocarbon sulfonate type cation-exchange membrane (produced by DuPont and marketed under trademark designation of "Nafion 117") 5×10 cm in area and 178 μm in thickness was roughened by sand blast, heated in an aqueous HCl solution (1+4) at 90° C., then boiled in distilled water to be converted to the $H^+$ form, and dried at 60° C.

Then, using a 300-mesh screen containing about 50% of a non-printing part, a resist ink of the following composition was applied in a thickness of 20 μm on the aforementioned cation-exchange membrane.

| Epoxy acrylate | 45 parts by weight |
| --- | --- |
| Diacrylate | 15 parts by weight |
| Methyldiethanolamine | 10 parts by weight |
| Benzophenone | 2 parts by weight |
| Thioxanthone | 0.2 parts by weight |
| Precipitated barium sulfate | 30 parts by weight |
| Phthalocyanin blue | 2 parts by weight |
| Aerosil | 2 parts by weight |
| Butyl cellosolve | 2% by weight |

Then the membrane was exposed to the light from a high-pressure mercury vapor lamp at 80 W/cm, for 5 seconds to cure the applied layer of the resist ink. Subsequently, the rear side of the cation-exchange membrane was similarly subjected to screen printing and exposure to the ultraviolet light. Thus, masks of a shape were formed on the opposite sides of the cation-exchange membrane.

The cation-exchange membrane which had undergone the treatment mentioned above was immersed in a platinum-ammine complex salt solution (platinum content 50 mg/100 ml) for 3 hours, washed with water, and placed in a 0.05 N $NaBH_4$ solution to be reduced therein at 40° to 50° C. for 2 hours. Consequently, a platinum layer was deposited in a thickness of 0.5 to 1 μm.

Then, the membrane was immersed in a platinum plating bath of the following composition at 50° to 60° C. for 2 hours, to give rise to a platinum layer 3 to 5 μm in thickness.

| Dinitrodiammine platinum | 0.5 g |
| --- | --- |
| Aqua ammonia (28%) | 50 ml |
| Water | 250 ml |
| Hydroxylamine hydrochloride (50%) | 10 ml |
| Hydrazine monohydrate (80%) | 5 ml |
| Water Amount to give a total volume of | 400 ml |
| pH | 11.7 |

After the formation of the platinum layer, the cation-exchange membrane was immersed in 10% NaOH and, with a few drops of 30% $H_2O_2$ added thereto, boiled for 1 hour to effect separation of the resist ink.

Then, the cation-exchange membrane was heated in a (1+4) HCl aqueous solution at 90° C. for 20 minutes, boiled in distilled water to effect conversion of the membrane to the $H^+$ form, and dried at a temperature not exceeding 60° C. Consequently, a moisture-sensitive element was obtained.

EXAMPLE 2

The same cation-exchange membrane as used in Example 1 was subjected to sand blast, immersion in hydrochloric acid, boiling in distilled water, and drying by following the procedure of Example 1.

Then, through a screen containing about 50% of nonprinting part, a resist ink of the following composition was deposited on one side of the cation-exchange membrane. The deposited layer of the resist ink was dried in the same manner as in Example 1.

| Oligoester acrylate | 20 parts by weight |
| --- | --- |
| Urethane acrylate | 20 parts by weight |
| 1,6-Hexane diol acrylate | 10 parts by weight |
| Benzoin alkyl ether | 2.5 parts by weight |
| Precipitated barium sulfate | 30 parts by weight |
| Phthalocyan blue | 2 parts by weight |
| Mercapto benzothiazol | 0.1 parts by weight |

The cation-exchange membrane which had undergone the treatment described above was immersed in a rhodium-ammine complex salt $(Rh(NH_3)_6)^{3+}$ solution at room temperature for 5 hours, washed with water, placed in a 0.05% $NaBH_4$ solution to be reduced therein at 40° to 50° C. for 2 hours, to induce deposition of a rhodium layer about 1 μm in thickness. It was then treated with a solution of the following composition at 60° to 70° C. for 2 hours, to give rise to a rhodium plated layer 5 μm in thickness.

| $(Rh(NH_3)_6)Cl_3$ | 0.12 g |
| --- | --- |
| $NH_2OH.HCl$ | 0.1 g |
| $N_2H_4.H_2O$ | 1 ml |
| $NH_4OH$ (28%) | 5 ml |
| Water | 100 ml |

After the plating was completed, the separation of the resist ink and the conversion to the $H^+$ form were carried out by following the procedure of Example 1. Consequently, there was obtained a moisture-sensitive element having 50% of the entire surface of the cation-exchange membrane exposed on one side and having a rhodium electrode layer formed throughout the entire surface of the cation-exchange membrane on the other side.

TEST EXAMPLE 1

(Determination of humidity with moisture-sensitive element produced by this invention)

The moisture-sensitive elements obtained in Example 1 and Example 2 were cut into pieces 5×10 mm. Platinum wires 1 mm in diameter were press welded as terminals one each to the opposite sides of each moisture-sensitive element. The elements were set in place in a test room and used for determination of humidity. The humidity was adjusted by mixing air moistened to saturation with dry air at a fixed ratio.

A potentiostat was used for the measurement of applied voltage and magnitude of flowing current. The relation between the relative humidity and the current density was found at 30° C., with the applied voltage varied to 3.5, 5.0, and 10.0 V. The results are shown in FIG. 3. The element of Example 1 and that of Example 2 produced equal results. In all the test runs using 3.5 V, 5.0 V, and 10.0 V of applied voltage, a satisfactory linear relation was recognized between the relative humidity and the current density.

TEST EXAMPLE 2

The moisture-sensitive elements of Example 1 and Example 2, and a moisture-sensitive element having rhodium electrodes formed one each on the opposite sides of a cation-exchange membrane without masking the membrane surface with any resin ink were cut into pieces 5×10 mm, with platinum wires press welded thereto in the same manner as in Test Example 1. These moisture-sensitive elements were first set in place in a test room having a relative humidity of 30% and then moved into another test room having a relative humidity of 80% to find variation in current under an applied voltage of 3.5 V. The results are shown in FIG. 4. They were then moved from the test room having a relative humidity of 80% to the test room having a relative humidity of 30% to find variation in current under the same applied voltage of 3.5 V. The results are shown in FIG. 4. In the diagram, the part A represents the case using the moisture-sensitive element of Example 1, the part B the case using the moisture-sensitive element of Example 2, and the part C the case using the moisture-sensitive element having the electrode layer formed throughout the entire surface of the exchange membrane.

It is noted from FIG. 4 that during the test of increasing relative humidity, the current reached the equilibrium level in about 1 minute in the case using the moisture-sensitive element of Example 1 and the current reached the equilibrium level in about 2 minutes in the case using the moisture-sensitive element of Example 2. During the test of decreasing relative humidity, the current reached the equilibrium level in about 3 minutes in the case using the moisture-sensitive element of Example 1 and in about 4 minutes in the case using the moisture-sensitive element of Example 2. In contrast, the current reached the equilibrium level in about 10 minutes in the case using the moisture-sensitive element having electrodes formed one each on the opposite sides of a cation-exchange membrane. These results clearly indicate that the moisture-sensitive element obtained by the present invention excels in response characteristic.

What is claimed is:

1. A method for the production of a moisture sensitive element possessing on the surface thereof an electrode layer and a moisture-adsorbing portion, comprising the steps of:
   (a) applying on a portion of a surface of a perfluorosulfonate cation-exchange membrane a resist ink which comprises a prepolymer resin selected from the group consisting of epoxy acrylate, alkyd acrylate, polyester acrylate, polyol acrylate, polyether acrylate, oligoacrylate and polyurethane acrylate or a cut monomer selected from the group consisting of monoacrylates, diacrylates and a triacrylate selected from the group consisting of 1,6-hexanediol monoacrylate, cyclohexyl acrylate, 1,6-hexanediol acrylate, neopentyl glycol diacrylate, trimethylol propane triacrylate and pentaerythritol triacrylate, a photoinitiator and at least one extender, said resist ink being curable by ultraviolet light thereby forming a cured surface material which is soluble in an alkali and which is incapable of having any metal deposited thereon when metal is chemically plated on said cation-exchange membrane;
   (b) irradiating the surface of said cation-exchange membrane coated with said resist ink with ultraviolet light in a patterned fashion thereby selectively curing the applied layer of said resist ink;
   (c) chemically plating the surface of said cation-exchange membrane which has been irradiated thereby forming an electrode layer on the portion of said surface which does not have cured resist ink thereon; and
   (d) treating the surface of said cation-exchange membrane with an aqueous alkali solution thereby removing said cured resist ink therefrom and exposing the underlying surface of the cation-exchange membrane which forms the moisture adsorbing portion of said membrane.

2. The method of claim 1, wherein said cation-exchange membrane is in the form of a $H^+$ ion conductor.

3. The method of claim 1, wherein said cation-exchange membrane is roughened prior to application of said resist ink.

4. The method of claim 1, wherein said resist ink is incapable of forming any residual polar group in the deposited layer of resist ink after drying.

5. The method of claim 1, wherein said resist ink contains at least 0.02 to 0.5% by weight of a sulfur compound as an inhibitor.

6. The method of claim 1, wherein said ink is applied over 20 to 80% of the surface area of said cation-exchange membrane.

7. The method of claim 1, wherein the thickness of the applied metal electrode layer ranges from 1–5 μm.

8. The method of claim 1, wherein the aqueous alkali developing solution is an aqueous sodium hydroxide solution of a concentration of 2 to 5 N.

* * * * *